(12) United States Patent
Carlson et al.

(10) Patent No.: US 11,365,454 B2
(45) Date of Patent: Jun. 21, 2022

(54) SYSTEMS AND METHODS FOR PROCESSING LIGNOCELLULOSIC BIOMASS

(71) Applicant: POET Research, Inc., Sioux Falls, SD (US)

(72) Inventors: David Charles Carlson, Brandon, SD (US); Rodney Duane Pierson, Wentworth, SD (US); James Michael Geraets, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 821 days.

(21) Appl. No.: 16/142,321

(22) Filed: Sep. 26, 2018

(65) Prior Publication Data

US 2019/0093184 A1    Mar. 28, 2019

Related U.S. Application Data

(60) Provisional application No. 62/563,414, filed on Sep. 26, 2017.

(51) Int. Cl.
| | |
|---|---|
| *C12M 3/00* | (2006.01) |
| *C12P 19/00* | (2006.01) |
| *C13K 1/02* | (2006.01) |
| *C12P 19/02* | (2006.01) |
| *C12P 19/14* | (2006.01) |

(Continued)

(52) U.S. Cl.
CPC ............... *C13K 1/02* (2013.01); *C12M 1/00* (2013.01); *C12M 21/12* (2013.01); *C12M 33/12* (2013.01); *C12M 41/40* (2013.01); *C12M 43/00* (2013.01); *C12M 43/04* (2013.01); *C12M 45/02* (2013.01); *C12M 45/06* (2013.01); *C12M 45/09* (2013.01); *C12M 45/20* (2013.01); *C12P 7/10* (2013.01);

(Continued)

(58) Field of Classification Search
CPC ........................................................ C08H 8/00
See application file for complete search history.

(56) References Cited

U.S. PATENT DOCUMENTS

| | | |
|---|---|---|
| 2,876,098 A | 3/1959 | Schandroch |
| 4,278,471 A | 7/1981 | Whittingham |

(Continued)

FOREIGN PATENT DOCUMENTS

| | | |
|---|---|---|
| WO | 2006128304 A1 | 12/2006 |
| WO | 2007051269 A1 | 5/2007 |

(Continued)

OTHER PUBLICATIONS

International Search Report for International Application No. PCT/US2018/052835, dated Feb. 11, 2019 (8 pages).

(Continued)

*Primary Examiner* — Nathan A Bowers
(74) *Attorney, Agent, or Firm* — Kagan Binder, PLLC

(57) ABSTRACT

The present disclosure includes systems and methods for hydrolyzing (e.g., pretreatment and/or enzymatic hydrolysis) lignocellulosic biomass into one or more sugars such as pentose and glucose sugars. The present disclosure includes configurations that incorporate flashing and/or liquid cooling so as to permit desirable throughput. The present disclosure also includes a liquefaction configuration so as to permit desirable (e.g., continuous high volume) throughput.

20 Claims, 10 Drawing Sheets

(51) Int. Cl.
*C12M 1/00* (2006.01)
*C12M 1/26* (2006.01)
*C12P 7/10* (2006.01)
*C12M 1/33* (2006.01)
*C12M 1/34* (2006.01)

(52) U.S. Cl.
CPC ............... *C12P 19/02* (2013.01); *C12P 19/14* (2013.01); *C12P 2201/00* (2013.01)

(56) References Cited

U.S. PATENT DOCUMENTS

| | | |
|---|---|---|
| 4,316,748 A | 2/1982 | Rugg et al. |
| 4,427,453 A | 1/1984 | Reitter |
| 4,436,586 A | 3/1984 | Elmore |
| 4,612,286 A | 9/1986 | Sherman et al. |
| 5,089,086 A | 2/1992 | Silander |
| 5,338,366 A | 8/1994 | Grace et al. |
| 5,366,558 A * | 11/1994 | Brink ............... C13K 1/04 127/43 |
| 5,424,417 A | 6/1995 | Torget et al. |
| 5,705,369 A | 1/1998 | Target et al. |
| 5,882,477 A | 3/1999 | Laakso et al. |
| 5,916,780 A | 6/1999 | Foody et al. |
| 6,022,419 A | 2/2000 | Torget et al. |
| 6,090,595 A | 7/2000 | Foody et al. |
| 6,106,668 A | 8/2000 | Stromberg et al. |
| 6,174,411 B1 | 1/2001 | Laakso et al. |
| 6,203,662 B1 | 3/2001 | Snekkenes et al. |
| 6,447,645 B1 | 9/2002 | Barrett et al. |
| 6,841,042 B2 | 1/2005 | Stromberg et al. |
| 7,666,637 B2 | 2/2010 | Nguyen |
| 7,807,419 B2 | 10/2010 | Hennessey et al. |
| 8,017,820 B2 | 9/2011 | Foody et al. |
| 8,057,639 B2 | 11/2011 | Pschorn et al. |
| 8,187,849 B2 | 5/2012 | Larsen |
| 8,246,750 B2 | 8/2012 | Shin et al. |
| 8,318,461 B2 | 11/2012 | Tolan et al. |
| 8,426,158 B2 | 4/2013 | Xu et al. |
| 8,450,094 B1 | 5/2013 | Narendranath et al. |
| 8,512,512 B2 | 8/2013 | Pschorn et al. |
| 8,518,213 B2 | 8/2013 | Retsina et al. |
| 8,597,431 B2 | 12/2013 | McDonald et al. |
| 8,685,167 B2 | 4/2014 | Retsina et al. |
| 8,685,685 B2 | 4/2014 | Retsina et al. |
| 8,703,453 B2 | 4/2014 | Larsen |
| 8,900,370 B2 | 12/2014 | Nguyen et al. |
| 8,906,657 B2 | 12/2014 | Retsina et al. |
| 8,911,557 B2 | 12/2014 | Nguyen et al. |
| 8,916,644 B2 | 12/2014 | Tamura et al. |
| 8,980,599 B2 | 3/2015 | Tolan et al. |
| 9,010,522 B2 | 4/2015 | Burke et al. |
| 9,085,484 B2 | 7/2015 | Guilfoyle et al. |
| 9,115,214 B2 | 8/2015 | Nguyen et al. |
| 9,127,325 B2 | 9/2015 | Nguyen et al. |
| 9,139,857 B2 | 9/2015 | Retsina et al. |
| 9,150,936 B2 | 10/2015 | Dottori et al. |
| 9,187,862 B2 | 11/2015 | Dottori et al. |
| 9,193,982 B2 | 11/2015 | Sjoede et al. |
| 9,221,734 B2 | 12/2015 | Monclin |
| 9,260,818 B2 | 2/2016 | Shin et al. |
| 9,290,821 B2 | 3/2016 | Blackbourn et al. |
| 9,315,750 B2 | 4/2016 | Retsina et al. |
| 9,333,468 B2 | 5/2016 | Nguyen et al. |
| 9,334,545 B2 | 5/2016 | McDonald et al. |
| 9,335,043 B2 | 5/2016 | Nguyen |
| 9,371,612 B2 | 6/2016 | Leavitt et al. |
| 9,528,084 B2 | 12/2016 | Romero et al. |
| 9,528,135 B2 | 12/2016 | Romero et al. |
| 9,631,316 B2 | 4/2017 | Retsina et al. |
| 9,738,729 B2 | 8/2017 | Retsina et al. |
| 9,758,843 B2 | 9/2017 | Larsen et al. |
| 9,816,644 B2 | 11/2017 | Tarpy et al. |
| 9,902,982 B2 | 2/2018 | Monclin et al. |
| 9,932,707 B2 | 4/2018 | Dottori et al. |
| 9,963,823 B2 | 5/2018 | Radigan, II et al. |
| 2001/0023748 A1 | 9/2001 | Marcoccia et al. |
| 2003/0199049 A1 | 10/2003 | Nguyen et al. |
| 2004/0060673 A1 | 4/2004 | Phillips et al. |
| 2005/0284592 A1 | 12/2005 | Jiang et al. |
| 2006/0154352 A1 * | 7/2006 | Foody ............... C12P 19/04 435/161 |
| 2008/0142181 A1 | 6/2008 | Sabourin |
| 2008/0293114 A1 * | 11/2008 | Foody ............... C12P 19/14 435/165 |
| 2010/0233771 A1 | 9/2010 | McDonald et al. |
| 2011/0281298 A1 | 11/2011 | Rawls et al. |
| 2013/0065289 A1 | 3/2013 | Carlson |
| 2014/0087432 A1 | 3/2014 | Nguyen et al. |
| 2015/0128933 A1 | 5/2015 | Larsen et al. |
| 2015/0191758 A1 | 7/2015 | Larsen et al. |
| 2015/0240198 A1 * | 8/2015 | Romero ............... C12P 19/14 435/286.1 |
| 2015/0284754 A1 | 10/2015 | Nguyen et al. |
| 2016/0069902 A1 | 3/2016 | Albitar et al. |
| 2016/0333519 A1 | 11/2016 | Radigan, II et al. |
| 2018/0355303 A1 * | 12/2018 | Rowland ............... C08H 8/00 |

FOREIGN PATENT DOCUMENTS

| | | |
|---|---|---|
| WO | 2009108773 A2 | 9/2009 |
| WO | 2011028554 A1 | 3/2011 |
| WO | 2016094877 A2 | 6/2016 |
| WO | 2016145527 A1 | 9/2016 |

OTHER PUBLICATIONS

Schell et al., "Dilute-Sulfuric Acid Pretreatment of Corn Stover in Pilot-Scale Reactor", Applied Biochemistry and Biotechnology, vol. 105-108, pp. 69-85, 2003, (19 pages).

* cited by examiner

SYSTEMS AND METHODS FOR PROCESSING LIGNOCELLULOSIC BIOMASS

CROSS REFERENCE TO RELATED APPLICATION

This application claims the benefit of U.S. Provisional Patent Application Ser. No. 62/563,414, filed Sep. 26, 2017, wherein the entire disclosure of said application is incorporated herein by reference.

FIELD

The present disclosure is related to processing lignocellulosic biomass, e.g., for a biochemical fermentation process. More particularly, the present disclosure is related to processing lignocellulosic biomass (e.g., modifying the structure thereof and/or transporting) through pretreatment and/or enzymatic hydrolysis.

BACKGROUND

Producing one or more biochemicals from lignocellulosic biomass can involve producing component sugars (e.g., xylose and/or glucose) from the biomass via pretreatment and/or enzymatic hydrolysis. One or more of the component sugars may then be converted into one or more biochemicals, e.g., via fermentation.

There is a continuing need to provide methods and systems to improve the throughput of lignocellulosic biomass through pretreatment and/or enzymatic hydrolysis, especially on a commercial-scale and continuous basis.

SUMMARY

The present disclosure includes embodiments of a system configured to process lignocellulosic biomass, wherein the system includes:
 a) a source of lignocellulosic biomass;
 b) an pretreatment system in fluid communication with the source of lignocellulosic biomass, wherein the pretreatment system includes at least one reactor configured to expose the lignocellulosic biomass to conditions to form a pretreated composition comprising a liquid component and a solid component, wherein the reactor has a discharge outlet and the pretreated composition at the discharge outlet is at conditions comprising a pressure above the saturated vapor pressure of the pretreated composition, and a total solids content of 10 to 35 percent; and
 c) at least one flash tank system in fluid communication with the pretreatment system, wherein the flash tank system includes a pressure reducing device coupled to a flash tank, wherein the pressure reducing device is configured to flash the pretreated composition from the conditions at the discharge outlet to a pressure less than the saturated vapor pressure of the pretreated composition at the discharge outlet, wherein the pretreated composition has less than three percent by volume of vapor space at least from the discharge outlet of the at least one reactor to an inlet of the pressure reducing device.

In some embodiments, the pretreated composition has less than one percent by volume of vapor space at least from the discharge outlet of the at least one reactor to an inlet of the pressure reducing device.

The present disclosure also includes embodiments of a method of processing lignocellulosic biomass, wherein the method includes:
 a) providing a pretreatment system;
 b) continuously supplying the lignocellulosic biomass to the pretreatment system, wherein the lignocellulosic biomass includes hemicellulose, cellulose, and lignin;
 c) pretreating the lignocellulosic biomass to form a pretreated composition including a liquid component and a solid component, wherein the pretreated composition is at conditions including a pressure above the saturated vapor pressure of the pretreated composition, and a total solids content of 10 to 35 percent; and
 d) flowing the pretreated composition through a closed pathway from the pretreatment system to a pressure reducing device to flash at least a portion of the pretreated composition so that at least a portion of the liquid component evaporates, wherein the pretreated composition in the closed pathway has less than three percent by volume of vapor space.

In some embodiments, the pretreated composition in the closed pathway has less than one percent by volume of vapor space.

The present disclosure also includes embodiments of a system configured to process lignocellulosic biomass, wherein the system includes:
 a) a source of a pretreated composition derived from lignocellulosic biomass;
 b) a liquefaction system, wherein the liquefaction system is in fluid communication with the pretreated composition, wherein the liquefaction system includes an inlet and is configured to enzymatically hydrolyze at least a portion of the pretreated composition to form a liquefied composition, wherein the liquefaction system includes two or more liquefaction tanks connected in series so that the contents of an upstream liquefaction tank feeds an adjacent downstream liquefaction tank, wherein the residence time of the pretreated composition in the two or more liquefaction tanks is at least 2 hours;
 c) at least one separation device in fluid communication with the liquefied composition, wherein the separation device is configured to separate at least a portion of the liquefied composition into a solid fraction and a liquid fraction; and
 d) at least one heat exchanger system in fluid communication with at least a first portion of the liquid fraction, wherein the heat exchanger system is configured to cool the first portion of the liquid fraction to a temperature that is sufficient to cool the pretreated composition provided to the liquefaction system to a temperature that permits enzymatic hydrolysis in the liquefaction system, and recycle the cooled first portion of the liquid fraction so that the cooled first portion of the liquid fraction is combined with the pretreated composition provided to the liquefaction system.

The present disclosure also includes embodiments of a method for liquefying lignocellulosic biomass, wherein the method includes:
 a) providing a source of a pretreated composition derived from lignocellulosic biomass;
 b) liquefying at least a portion of the pretreated composition to form a liquefied composition, wherein the liquefying includes passing the pretreated composition through two or more liquefaction tanks connected in series, wherein the residence time of the pretreated composition in the two or more liquefaction tanks is at least 2 hours;
 c) separating at least a portion of the liquefied composition into a solid fraction and a liquid fraction; and d) cooling at least a portion of the liquid fraction to a temperature that is sufficient to cool the pretreated composition that is provided in step (a) to a temperature that permits enzymatic hydrolysis, and e) combining the cooled liquid fraction in step (d) with an additional portion of pretreated composition provided in step (a).

DETAILED DESCRIPTION

Figure 2:
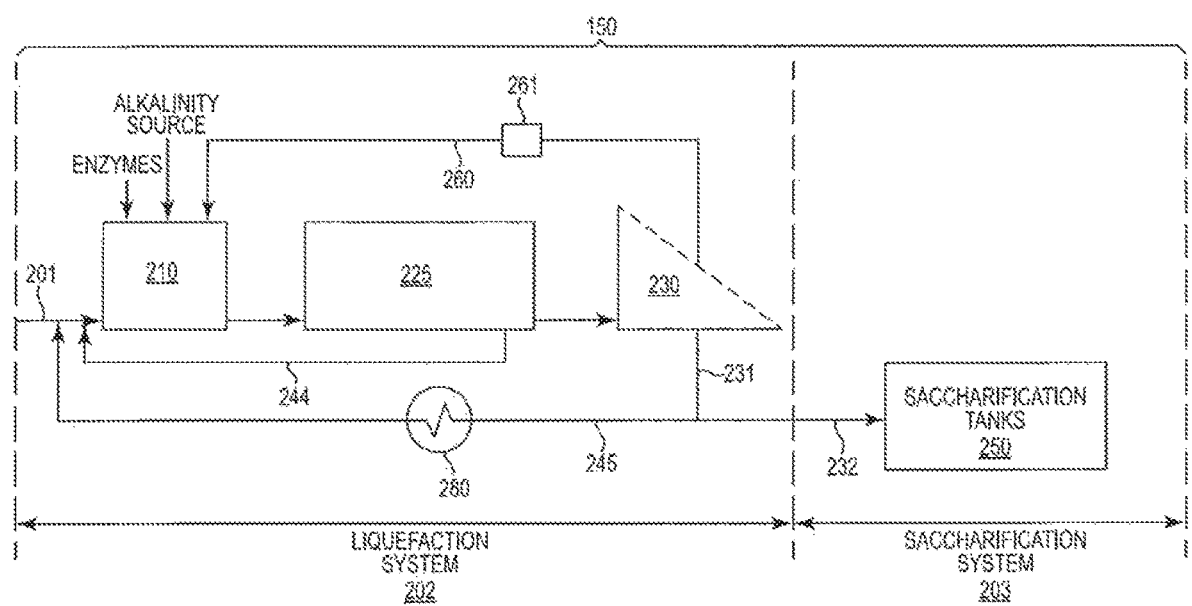
FIG. 2 shows a schematic of an exemplary enzymatic hydrolysis system in FIGS. 1A and 1B.
Figure 3:
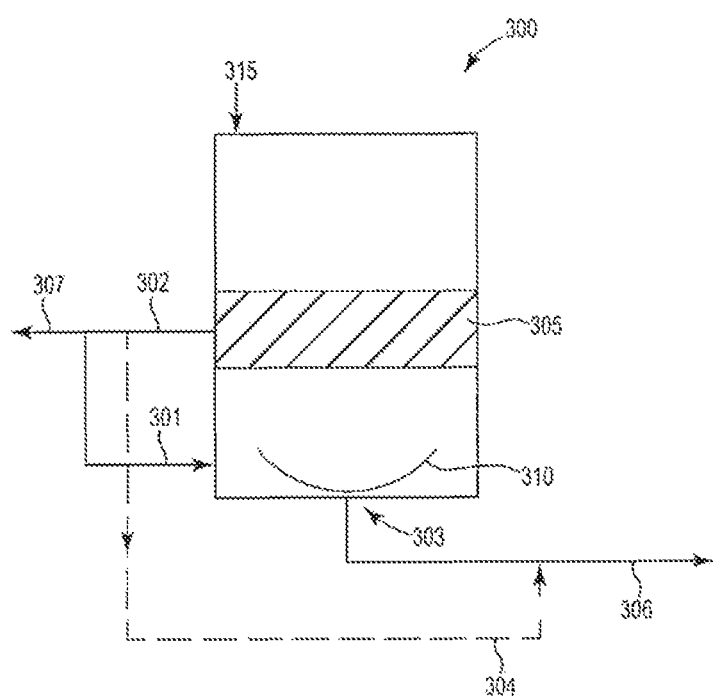
FIG. 3 shows a schematic illustration of an exemplary vertical acid hydrolysis reactor.

Disclosed in embodiments herein are systems and methods for processing lignocellulosic biomass to be used in a fermentation process. For illustration purposes, FIGS. 1-3 are referred to in describing systems and methods for processing lignocellulosic biomass, e.g., for a downstream fermentation process.

In fermentation processes, lignocellulosic biomass can be used as a source of one or more monosaccharides that can be converted to one or more biochemicals using one or more microorganisms. Monosaccharides can be made available by processing the lignocellulosic biomass using one or more techniques such as pretreatment, enzymatic hydrolysis, and the like, which are discussed in detail below. Lignocellulosic biomass includes materials such as grasses, wood chips and pulp, various cereal straws, including corn stover (e.g., corn cobs, stalks, husks and leaves) made available during or after harvesting of the corn kernels, fiber from the corn kernel, and other plant matter (grown for processing into bioproducts or for other purposes). Lignocellulosic biomass includes hemicellulose, cellulose, and lignin.

As used herein, "pretreatment" refers to a variety of chemical, mechanical, and/or thermal techniques that at least partially breakdown the physical and chemical structure of lignocellulosic biomass. Nonlimiting examples of pretreatment include alkaline hydrolysis, acid hydrolysis, and the like.

Before pretreatment, a lignocellulosic biomass feedstock can be prepared by a variety of techniques such as size reduction, washing, contacting with steam, combinations of these, and the like. For example, a biomass lignocellulosic feedstock can be prepared prior to acid hydrolysis by grinding the lignocellulosic biomass feedstock in one or more grinders (not shown) into ground solids to reduce the size of the feedstock and increase its surface area for contact with a hydrolysis medium.

In some embodiments, the lignocellulosic biomass fed as a feedstock to pretreatment includes ground corn stover having a particle size such that at least 80 percent of the ground corn stover passes through a six inch screen and less than 20 percent of the ground corn stover passes through a 0.125 inch screen.

For illustration purposes, acid hydrolysis is specifically referred to merely as an example of pretreatment according to the present disclosure.

Figure 1A:
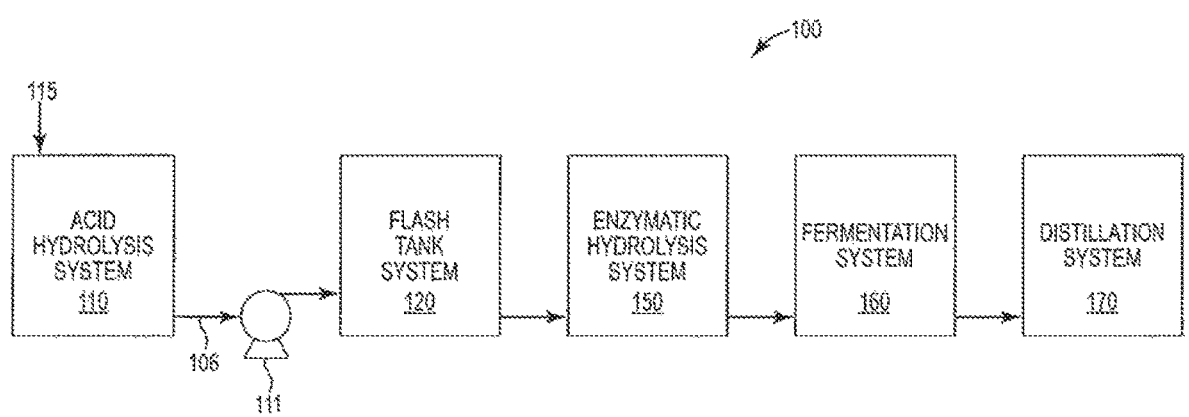
FIG. 1A shows a schematic of an exemplary system according to the present disclosure for processing lignocellulosic biomass for a fermentation process.
Figure 1B:
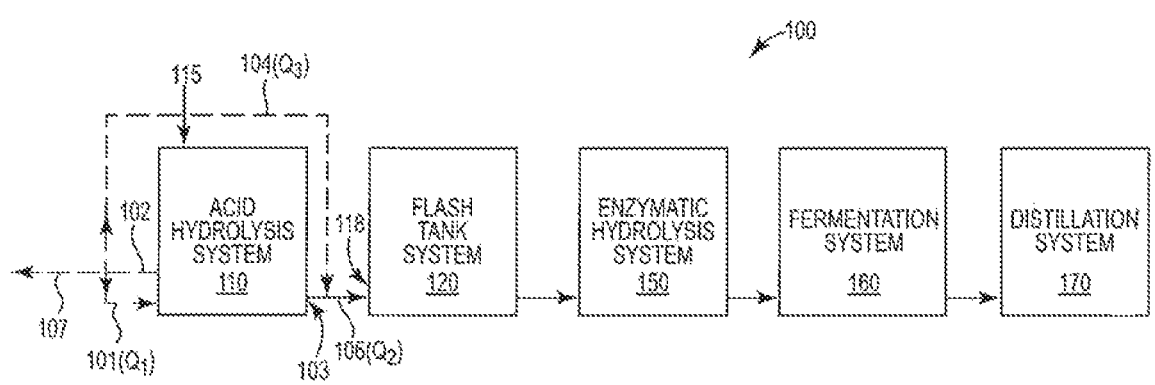
FIG. 1B shows an optional schematic of the exemplary system shown in FIG. 1A.

As shown in FIGS. 1A and 1B, system 100 includes an acid hydrolysis system 110. An acid hydrolysis system can be in fluid communication with a source of lignocellulosic biomass to receive the lignocellulosic biomass, e.g., in a continuous manner. For example, piping and one or more pumps (not shown) can couple the acid hydrolysis system 110 to a source of lignocellulosic biomass so that the acid hydrolysis system can receive the lignocellulosic biomass. Acid hydrolysis system 110 includes an inlet 115 to receive the lignocellulosic biomass feedstock (e.g., as a slurry that includes ground lignocellulosic biomass and water). In some embodiments, an acid hydrolysis system can include at least one acid hydrolysis reactor configured to expose (contact) the lignocellulosic biomass to an aqueous acid solution to form a pretreated composition. As used herein, a "pretreated composition" is derived from at least partial acid hydrolysis of a polysaccharide in a lignocellulosic biomass material into oligosaccharides and/or monosaccharides. For example, a polysaccharide such as hemicellulose can be hydrolyzed into one or more of its component monosaccharides including, e.g., a pentose such as xylose. A pretreated composition can include a solid component and a liquid component. In some embodiments, the solid component can include solid, unhydrolyzed materials of a biomass feedstock such as lignin, cellulose, and/or hemicellulose. In some embodiments, the liquid component can be a liquid hydrolysate (or liquor) and can include water, one or more monosaccharides (e.g., at least xylose) and byproducts of hydrolysis such as fermentation inhibitors. Examples of fermentation inhibitors include furfural, hydroxymethylfurfural (HMF), phenol compounds, compositions thereof, and the like. In some embodiments, a pretreated composition includes at least xylose, furfural, cellulose and lignin. In some embodiments, a pretreated composition can also include one or more hexoses such as glucose.

During acid hydrolysis, the "severity" can be adjusted by varying one or more of time period, temperature, and pH during hydrolysis. In some embodiments, during acid hydrolysis an aqueous acid solution can have a pH in the range from 0.5 to 5, from 0.5 to 3, from 1 to 2.5, or even from 1.5 to 2. The aqueous acid solution can include an acid such as sulfuric acid present in a concentration in the range from 0.2 to 1.3% w/w, or even 0.5 to 1% w/w. In some embodiments, acid hydrolysis can be performed for a time period in a range from 15 minutes to 5 hours, or even 30 minutes to 4 hours. In some embodiments, acid hydrolysis can be performed at a temperature in the range from greater than 230° F. to 280° F., or even from 245° F. to 275° F. In some embodiments, acid hydrolysis can be performed at pressure in the range from 20 to 80 psig, or even 40 to 70 psig. Hydrolyzing lignocellulosic biomass to provide, e.g., xylose and/or glucose is described in, e.g., U.S. Pat. No. 5,424,417 (Torget et al.); U.S. Pat. No. 6,022,419 (Torget et al.); and U.S. Pat. No. 8,450,094 (Narendranath et al.), and U.S. Publication Number 2010/0233771 (McDonald et al.), wherein the entireties of said patent documents are incorporated herein by reference for all purposes.

Operating at a severity as described herein can help provide the pretreated composition at the acid hydrolysis reactor discharge outlet with a desirable total solids content. As used herein, "total solids content" means the total content of dissolved and suspended solids based on the total weight of the composition (e.g., pretreated composition). In some embodiments, the pretreated composition at the acid hydrolysis reactor discharge outlet can have a total solids content from 10 to 35 percent, from 10 to 30 percent, from 15 to 30 percent, or even from 15 to 25 percent. In some embodiments, having a relatively higher solids content within and near the bottom of an acid hydrolysis reactor can advantageously permit the undissolved solids to physically interact with other undissolved solids and facilitate physically breaking down the lignocellulosic biomass. Because the pretreated composition may be diluted with cooling liquid (e.g., water) after flashing and prior to enzymatic hydrolysis, providing the pretreated composition with a relatively high solids content as described herein permits the pretreated composition to be cooled with dilution liquid while at the same time providing a solids content during enzymatic hydrolysis that is sufficiently high to result in commercially desirable ethanol titers.

As mentioned above, the lignocellulosic biomass feedstock can be present in a pretreatment system (e.g., acid hydrolysis system) as a slurry that includes ground lignocellulosic biomass feedstock and an aqueous liquid (e.g., water and acid). In some embodiments, the pretreated composition has less than 3 percent by volume of vapor space, less than 2 percent by volume of vapor space, less than one percent by volume of vapor space, less than 0.5 percent by volume of vapor space, or even less than 0.25 percent by volume of vapor space at least from the discharge outlet of a pretreatment reactor to a pressure reducing device where the slurry of pretreated composition flashes to a reduced pressure so that at least a portion of the liquid in the slurry flashes from a liquid phase to a gas phase. As used herein, the "vapor space" of the pretreated composition refers to gas that may present in the space surrounding solid lignocellulosic biomass that is present in the pretreated composition, which is flowing (e.g., in a closed pathway such as a pipe system) from the pretreatment reactor to a valve or nozzle where the pretreated composition flashes from reactor conditions to conditions having a lower or reduced pressure (e.g., atmospheric conditions or vacuum conditions). A pretreated composition with a relatively low vapor space as described herein has essentially all liquid surrounding the undissolved lignocellulosic biomass so that the pretreated composition is a slurry. The vapor space as described herein does not refer to gas (e.g., air) that may be present (entrapped) in closed particles of biomass. The slurry of pretreated composition can be transferred from the discharge of a pretreatment reactor to a pressure reducing device via piping, which is a closed system. This is in contrast to a lignocellulosic biomass that may be present in a pipe and has essentially all gas, such as steam vapor, surrounding the lignocellulosic biomass. Having liquid rather than vapor in the space surrounding the solid biomass can facilitate transferring the solid biomass downstream.

The pretreated composition leaving a pretreatment system such as the acid hydrolysis system 110 can be at a variety of pressure and temperature conditions. For example, the pretreated composition at the discharge outlet of an acid hydrolysis reactor can be at a pressure above the saturated vapor pressure of the pretreated composition. Providing and maintaining the pretreated composition at a pressure above its saturated vapor pressure can facilitate subsequent flashing operations to a lower pressure such as a pressure that is below the saturated vapor pressure of the pretreated composition at the discharge outlet of the acid hydrolysis reactor (e.g., atmosphere or vacuum conditions). Providing and maintaining the pretreated composition at a pressure above its saturated vapor pressure at the discharge outlet of the acid hydrolysis reactor is consistent with the relatively low vapor space that is present as described above. Because the pretreated composition is at a pressure above its saturated vapor pressure at the discharge outlet of the acid hydrolysis reactor any water present in the pretreated composition will be present in liquid form and not in vapor form. "Flashing" the pretreated composition from a pressure above its saturated vapor pressure at the discharge outlet of the acid hydrolysis reactor to a pressure below its saturated vapor pressure at the discharge outlet of the acid hydrolysis reactor can facilitate evaporative cooling. As used herein, "evaporative cooling" refers to cooling of the pretreated composition when at least a portion of the liquid component of the pretreated composition (e.g., liquid water carrier in the pretreated composition that helps form a slurry) changes phase from liquid phase to gas phase. The energy consumed in such a phase change can cause the remaining pretreated composition to cool down to a lower temperature.

In some embodiments, the pretreated composition at the discharge outlet of an acid hydrolysis reactor can be at a pressure in the range from 20 to 80 psig, from 40 to 70 psig, or even from 25 to 35 psig. In some embodiments, the pretreated composition at the discharge outlet of an acid hydrolysis reactor can be at a temperature greater than 212° F., e.g., in the range from 230° F. to 280° F., or even from 245° F. to 275° F. As discussed below, it can be desirable to discharge the pretreatment composition at reactor conditions without any cooling to facilitate subsequent flashing to a lower pressure to help disrupt the physical structure of the biomass for subsequent enzymatic hydrolysis. Any cooling that may be desired prior to enzymatic hydrolysis can be done during and/or after flashing.

Optionally, one or more aqueous streams can be added to the acid hydrolysis system and/or the pretreated composition discharged therefrom to help dilute the pretreated composition if desired, e.g., to help control solids content. For example, as shown in FIG. 1B, first aqueous stream 101 having a first flow rate (Q1) can be in fluid communication with an acid hydrolysis reactor in system 110 to dilute the pretreated composition inside the reactor and near the acid hydrolysis reactor discharge outlet (schematically shown as 103), if needed, so that the pretreated composition at the acid hydrolysis reactor discharge outlet has a desirable total solids content for subsequent processing. For example, if needed, the pretreated composition can be diluted so that it has a total solids content at the acid hydrolysis reactor discharge outlet from 10 to 35 percent, from 10 to 30 percent, or even from 15 to 30 percent. In some embodiments, having a relatively higher solids content within and near the bottom of an acid hydrolysis reactor can advantageously permit the undissolved solids to physically interact with other undissolved solids and facilitate physically breaking down the lignocellulosic biomass. The stream 101 can also help dilute the pretreated composition, if needed, near the bottom of the reactor so as to facilitate conveying the pretreated composition to the flash tank system 120 due to the presence of liquid and pressure. In some embodiments, the stream 101 can be "hot" to help maintain the pretreated composition at or near the temperature and pressure of the acid hydrolysis reactor so as to facilitate evaporative cooling and expansion when flashing the pretreated composition from reactor pressure to a lower pressure in flash tank system 120. In some embodiments, the temperature of the first aqueous stream 101 is in the range from 230° F. to 280° F., or even from 245° F. to 275° F., and at a pressure in the range from 20 to 80 psig, from 40 to 70 psig, or even from 25 to 35 psig. The flow rate (Q1) of first aqueous stream 101 can be controlled via a control valve. In some embodiments, the flow rate (Q1) of first aqueous stream 101 can be in the range from 0 to 1000 gallons per minute, from 0 to 500 gallons per minute, or even from 0 to 200 gallons per minute. In some embodiments, a control valve can completely restrict the flow rate (Q1) of first aqueous stream 101 so that the flow rate is zero.

Optionally, as illustrated in FIG. 1B, an acid hydrolysis reactor in acid hydrolysis system 110 can include at least one separation device disposed within the reactor interior to separate liquid from solid lignocellulosic biomass. A separation device can separate at least some liquid from solid lignocellulosic biomass in the reactor to form a liquid stream such as liquid stream 102. Because liquid stream 102 is at reactor temperature and pressure, at least a portion of liquid stream 102 can be used to form first aqueous stream 101. Advantageously, if needed, liquid from the acid hydrolysis reactor can be used as a readily available source to help keep the pretreated composition at or near reactor temperature when flashing the pretreated composition to a reduced pressure. Alternatively, a source of "hot" liquid could be provided from a source that is separate from the acid hydrolysis reactor but is not required. As shown in FIG. 1B, as the pretreated composition 106 flows from the acid hydrolysis system 110 into an inlet 118 of the flash tank system 120 the pretreated composition 106 has a second flow rate (Q2), where 0≤Q1<Q2. The second flow rate (Q2) of the pretreated composition 106 can be controlled via a control valve. In some embodiments, the second flow rate of the pretreated composition 106 into an inlet of the flash tank system 120 can be in the range from 100 to 1,500 gallons per minute, from 200 to 1,000 gallons per minute, from 250 to 750 gallons per minute, or even from 500 to 800 gallons per minute.

Referring to FIG. 1B, one or more additional liquid streams could be formed from liquid stream 102 such as liquid stream 107. In some embodiments, liquid stream 107 could be used for other purposes such as recirculated to help convey lignocellulosic biomass into reactor inlet 115. In some embodiments, at least a third aqueous stream 104 having a third flow rate (Q3) can be in fluid communication with the pretreated composition after the pretreated composition passes through a reactor outlet to dilute the pretreated composition so that the pretreated composition has a total solids content from 10 to 35 percent, from 10 to 30 percent, or even from 15 to 30 percent. As shown in FIG. 1B, at least a portion of liquid stream 102 can be used to form third aqueous stream 104. Advantageously, as previously mentioned, liquid from the acid hydrolysis reactor can be used as a readily available source to keep the pretreated composition at or near reactor temperature when flashing the pretreated composition to a reduced pressure. Alternatively, the third aqueous stream 104 having a third flow rate (Q3) could be provided from a source different than the acid hydrolysis reactor, but is not required. Diluting the pretreated composition with the third aqueous stream 104 can be used to help convey the pretreated composition to the flash tank system 120 due to the presence of liquid and pressure to avoid undue plugging of the pretreated composition. As with the temperature and pressure of the first aqueous stream 101, the temperature of the third aqueous stream 104 can be in the range from 230° F. to 280° F., or even from 245° F. to 275° F., and at a pressure in the range from 20 to 80 psig, from 40 to 70 psig, or even from 25 to 35 psig. In some embodiments, if a third aqueous stream 104 is used, its flow rate (Q3) can be calculated relative to the second flow rate (Q2) as follows: 0≤Q3<0.5*Q2, where Q2 is the sum of Q3 and the flow rate out of an acid hydrolysis reactor in system 110. In some embodiments, the flow rate of the third aqueous stream 104 can be in the range from 0 to less than 750 gallons per minute, from 0 to 500 gallons per minute, from 0 to 300 gallons per minute, or even from 0 to 200 gallons per minute.

It is noted that each of liquid streams 101, 102, 104, and 107 can have a liquid component and a solid component. In some embodiments, the solid component can include dissolved and undissolved solid lignocellulosic biomass materials. In some embodiments, the solid component can include relatively small, undissolved solid, unhydrolyzed materials of a biomass feedstock such as lignin, cellulose, and/or hemicellulose. The size of the solid particles in the liquid streams 101, 102, 104, and 107 can depend on the size of the screen openings in the screen of the separation device. In some embodiments, the liquid streams 101, 102, 104, and 107 can include water, products of hydrolysis such as one or more monosaccharides (e.g., xylose), undissolved solids that pass through the screen in a separation device, and byproducts of hydrolysis such as fermentation inhibitors. A separation device can be located above the discharge outlet 103 (e.g., near the top or middle of a reactor). Because a separation device can remove liquid from a reactor, the separation device can function as a dewatering device as well, thereby increasing the total solids concentration at the discharge outlet 103 unless otherwise diluted somehow (e.g., via stream 101).

Pretreatment (e.g., acid hydrolysis) can be performed in a variety of system and apparatus configurations. FIG. 3 shows a schematic illustration of an exemplary vertical acid hydrolysis reactor 300 that can be used in acid hydrolysis system 110. With respect to FIGS. 1B and 3, the stream 101 is the same as the stream 301, the stream 102 is the same as stream 302, the stream 104 is the same as the stream 304, and the stream 106 is the same as the stream 306, stream 107 is the same as stream 307, and inlet 115 is the same as inlet 315. As described above with respect to FIG. 1B, streams 301, 302, 304, and 307 are optional.

In some embodiments, as shown in FIG. 3, vertical acid hydrolysis reactor 300 has an inlet 315 to receive the lignocellulosic biomass feedstock (e.g., as a slurry that includes ground lignocellulosic biomass and water), where the inlet 315 is located proximal to the top of the acid hydrolysis reactor 300. The discharge outlet 303 is located proximal to the bottom of the of acid hydrolysis reactor 300. In a vertical reactor such as reactor 300, the weight of the reactor contents (lignocellulosic biomass and liquid medium) can increase the pressure of the pretreated composition near the discharge outlet 303, thereby increasing the total solids content (dissolved and suspended solids) near the discharge outlet 303. In some embodiments, the total solids content of the pretreated composition within reactor 300 and near the outlet 303 can be in the range from 10 to 35 percent, from 10 to 30 percent, or even from 15 to 30 percent. In some embodiments, having a relatively higher solids content within reactor 300 and near the discharge outlet 303 can advantageously permit the undissolved solids to physically interact with other undissolved solids and facilitate physically breaking down the lignocellulosic biomass. In some embodiments, the pretreated composition within reactor 300 and near discharge outlet 303 can be diluted (e.g. via stream 301) to adjust the solids content (e.g., to improve flowability). Also, if needed, the pretreated composition can be diluted (e.g., with via stream 304) after it passes through the discharge outlet to help convey the pretreated composition to a flash tank system. As shown in FIG. 3, at least a portion of liquid stream 302 can be used to form aqueous streams 301 and 304. Advantageously, liquid from the acid hydrolysis reactor can be used as a readily available source to keep the pretreated composition at or near reactor temperature when flashing the pretreated composition to atmosphere. Alternatively, the third aqueous stream 304 having a third flow rate (Q3) could be provided from a source different than the acid hydrolysis reactor, but is not required.

As shown in FIG. 3, vertical reactor has a separation device 305 including a screen (not shown) to separate and draw off liquid from relatively large particles of solid lignocellulosic biomass that can remain in reactor 300, thereby forming liquid stream 302. It is noted that liquid stream 302 can have a liquid component and a solid component. In some embodiments, the solid component can include dissolved and undissolved solid lignocellulosic biomass materials. In some embodiments, the solid component can include relatively small, undissolved solid, unhydrolyzed materials of a biomass feedstock such as lignin, cellulose, and/or hemicellulose. The size of the solid particles in the liquid stream 302 depends on the size of the screen openings in the screen of the separation device 305. In some embodiments, the liquid stream 302 can include water, products of hydrolysis such as one or more monosaccharides (e.g., xylose), undissolved solids that pass through the screen in separation device 305, and byproducts of hydrolysis such as fermentation inhibitors. The separation device 305 can be located above the discharge outlet 303 (e.g., near the top or middle of reactor 300). Because a separation device 305 can remove liquid from the reactor 300, the separation device can function as a dewatering device as well, thereby increasing the total solids concentration at the discharge outlet 303 unless otherwise diluted somehow (e.g., via stream 301).

In some embodiments, an acid hydrolysis reactor can include an agitation system comprising an agitation device located inside the reactor vessel and proximal to the discharge outlet to agitate the pretreated composition. For example, in the exemplary acid hydrolysis reactor 300 shown in FIG. 3, a rotational, agitation member 310 is coupled to the bottom of reactor 300 to help agitate the pretreated composition near the bottom of reactor 300 to facilitate conveying the pretreated composition out of reactor 300. In some embodiments, the agitation member can be configured such that agitation helps move at least a portion of undissolved biomass that may be in contact with the bottom of reactor 300. An example of an agitation device as described herein is illustrated in, e.g., U.S. Pat. No. 6,203,662 (Snekkenes et al.), which patent is incorporated herein by reference.

In some embodiments, because the total solids content near the agitation member 310 can be relatively high (e.g., about 10% or greater, about 25% or greater, even about 30% or greater) the agitation member 310 can advantageously function to shear undissolved solid material in the pretreated composition, thereby further breaking down the particle size of the solid material. Referring to FIG. 3, one or more additional liquid streams could be formed from liquid stream 302 such as liquid stream 307. In some embodiments, liquid stream 307 could be used for other purposes such as recirculated to help convey lignocellulosic biomass into reactor inlet 315. Vertical reactors having a separation device to separate liquid from solid lignocellulosic biomass are described in, for example, U.S. Pat. No. 5,089,086 (Silander) and U.S. Pat. No. 6,203,662 (Snekkenes et al.); and U.S. Pub. No. 2005/0284592 (Jiang et al.), which patents are incorporated herein by reference.

Optionally, one or more pumps 111 can be in fluid communication with the discharge outlet of an acid hydrolysis reactor, e.g., such as the acid hydrolysis reactor 300 in FIG. 3, to pump the pretreated composition to the flash tank system 120.

As shown in FIGS. 1A and 1B, at least one flash tank system 120 is in direct fluid communication with the acid hydrolysis system 110 with no process equipment in between acid hydrolysis system 110 and flash tank system 120. Direct fluid communication can provide a simple and effective technique for processing lignocellulosic biomass, especially when processing lignocellulosic biomass such as corn stover, which can be challenging to transport through process equipment in a continuous manner without undue plugging. As used herein, "direct" fluid communication means that the pretreated composition is transferred through piping and valves from acid hydrolysis system 110 to the pressure reducing device of flash tank system 120 with no process equipment in between other than instrumentation and one or more optional pumps.

Flash tank system 120 is configured to flash the pretreated composition from the conditions at the discharge outlet of a reactor in acid hydrolysis system 110 to a reduced pressure to cool at least a portion of the pretreated composition and so that the pretreated composition can be provided to enzymatic hydrolysis. A flash tank system can include one or more flash tanks connected in series or parallel. Also, a flash tank system 120 can include a pressure reducing device such as one or more valves or nozzles. For example, a valve or nozzle having an inlet can be coupled to an inlet of a flash tank (or cyclone) to allow a sudden decrease in pressure (flash) of the pretreated composition from reactor conditions to a lower pressure as pretreated composition passes through the valve and into the flash tank. Flashing can allow at least some of the liquid in the pretreated composition to change in phase from liquid to gas. Such phase change can utilize evaporative cooling to cool at least a portion (e.g., substantially all) of the remaining pretreated composition (liquid and solid). The liquid mentioned above that changes phase to gas refers both to the liquid medium that surrounds the exterior of undissolved, lignocellulosic biomass and to the liquid that is contained within the particles of undissolved, lignocellulosic biomass.

Figure 1C:
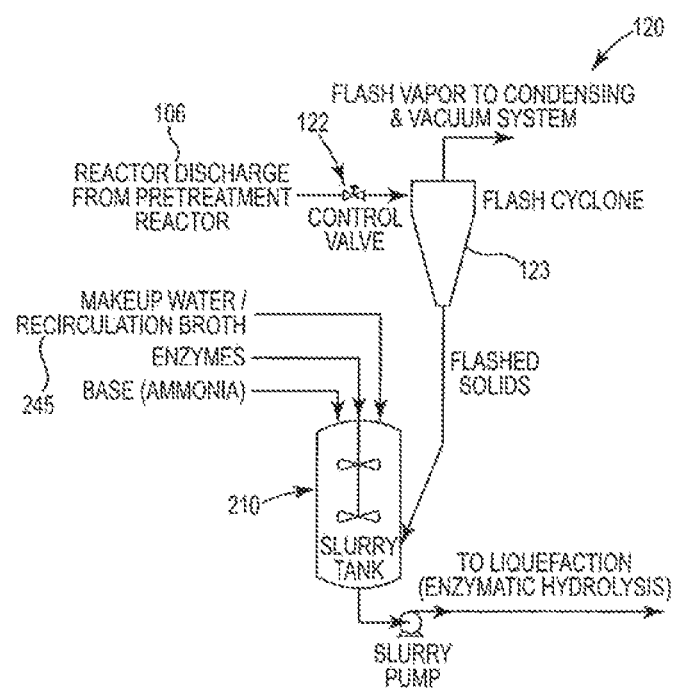
FIG. 1C shows a schematic illustration of an embodiment of a flash tank system according to the present disclosure.

An example of a flash tank system 120 is illustrated in FIG. 1C. As shown, a pretreated composition in reactor discharge 106 (from acid hydrolysis system in FIGS. 1A and 1B) can pass directly to flash tank system 120 and enter a control valve 122 where the pretreated composition can flash to a reduced pressure as described herein and into a flash tank (flash cyclone) 123. At least some liquid in the pretreated composition can change phase to vapor and vent through the top of flash cyclone 123. If desired, the vapor can be condensed to recover heat energy. Also, if desired, a vacuum system (such as a liquid ring vacuum pump) may be used in order to operate the flash cyclone at pressures less than atmospheric pressure (further discussed below).

As shown in FIG. 1C, after the pretreated composition is flashed into flash cyclone 123, the pretreated composition can be transferred to slurry tank 210 (further discussed below) where it is combined with one or more cellulase enzymes, one or more ingredients to adjust pH (e.g., a basic substance such as ammonia), and make-up water. As also further discussed below, an example of make-up water includes cooled recirculation broth 245 from liquefaction.

The temperature to which the pretreated composition can be cooled can depend, at least in part, on the pressure in the flash tank. While a flash tank can be configured to operate at or near atmospheric pressure, in practice such a flash tank can operate at a pressure that is negative or positive to atmosphere pressure. In some embodiments a flash tank can have a pressure in the range from 5 psig to −14 psig, from 1 psig to −12 psig, from 0 psig to −10 psig, from −2 psig to −11 psig, or even from −8 psig to −11 psig. In some embodiments, the pretreated composition can be cooled in a flash tank due to flashing to a temperature of 230° F. or less, 220° F. or less, 212° F. or less, 205° F. or less, 200° F. or less, 190° F. or less, 180° F. or less, 170° F. or less, or even 160° F. or less (e.g., from 160° F. to 220° F.). Vapor and gas can be removed through the top of the flash tank and the remaining flashed pretreated composition can be removed from the bottom of the flash tank. In some embodiments, a flash tank is a cyclone separator, which allows vapor and gas to vent through the top and liquid to drain out of the bottom due to gravity. Advantageously, by utilizing flash cooling as described herein relatively less additional cooling need be performed after flash tank system 120, but prior to enzymatic hydrolysis, so that the enzymes in enzymatic hydrolysis are not exposed to a temperature that impacts the enzymes used in hydrolysis to an undue degree. Also, by relying at least in part on flash cooling, a desirable solids content can be provided to liquefaction even though some dilution with liquid occurs to additionally cool the pretreated composition prior to liquefaction. Further, providing the flash tank pressure with a negative pressure can cool the pretreated composition even more as compared to using atmospheric pressure, thereby further reducing the amount of cooling liquid that may be needed to sufficiently cool the pretreated composition for enzymatic hydrolysis, thereby diluting the solids content even less.

And, depending on the conditions of the pretreated composition (e.g., temperature and pressure) the sudden change in pressure of the pretreated composition that occurs in the flash tank system 120 can permit at least some disruption and breakdown of the solid material in the pretreated composition to increase its surface area and facilitate enzyme activity during enzymatic hydrolysis (liquefaction and saccharification). This is primarily due to the volume expansion that occurs due to the partial evaporation of liquid that is contained within the particles of undissolved, lignocellulosic biomass during flashing.

As yet another advantage, the configuration of the acid hydrolysis system 110 and flash tank system 120 as described herein can permit desirable throughput for materials on a continuous basis that can be difficult to otherwise process without undue clogging, bridging, and the like, while at the same time providing desirable sugar yields. For example, lignocellulosic biomass such as corn stover can be processed according to continuous commercial production schedules even with variations in upstream processes such as acid hydrolysis. For example, if corn stover is "over-treated" in acid hydrolysis system 110, then the pretreated corn stover can have a mud-like consistency, which can make transferring the pretreated corn stover through some process equipment challenging. Or, if corn stover is "under-treated" in acid hydrolysis system 110, then the pretreated corn stover can have a relatively rigid-like consistency, which can also make transferring the pretreated corn stover through some process equipment challenging. However, the configuration of the acid hydrolysis system 110 and flash tank system 120 as described herein can tolerate such variations. In some embodiments, the configuration of the acid hydrolysis system 110 and flash tank system 120 as described herein that includes a single acid hydrolysis reactor and a single flash tank can process 200 tons/day or more of ground corn cobs and ground corn stover, 500 tons/day or more of ground corn cobs and ground corn stover, or even 700 tons/day or more of ground corn cobs and ground corn stover. In some embodiments, a single acid hydrolysis reactor can have a volume in the range from 100,000 to 200,000 gallons (e.g., 150,000 gallons). In some embodiments a single acid hydrolysis reactor can be from 15 to 20 feet in diameter and from 120 to 130 feet in height. In some embodiments, a single flash cyclone can have a volume in the range from 500 to 4,000 gallons (e.g., 750 gallons). In some embodiments a single flash cyclone can have an outside diameter from 24 to 70 inches and a height from 10 to 30 feet.

As shown in FIGS. 1A and 1B, system 100 according to the present disclosure also includes an enzymatic hydrolysis system 150. As shown, enzymatic hydrolysis system 150 is in direct fluid communication with the flash tank system 120. In an enzymatic hydrolysis system 150, at least a portion of the cellulose in the pretreated composition from flash tank system 120 can be enzymatically hydrolyzed to hydrolyze at least a portion of cellulose into glucose. As described herein below, because enzymatic hydrolysis system 150 is in direct fluid communication with the flash tank system 120 the pretreated composition can avoid having to pass through a heat exchanger, if desired, before being transferred to enzymatic hydrolysis system 150. As described herein below, the temperature of the pretreated composition can be cooled to a temperature suitable for enzymatic hydrolysis via the flash tank system 120. For example, as described below, recirculated cooled liquid can be added to the pretreated composition prior to introducing enzymes for hydrolysis.

An example of an enzymatic hydrolysis system according to the present disclosure is illustrated in FIG. 2. As shown in FIG. 2, the enzymatic hydrolysis system 150 can include liquefaction system 202 and saccharification system 203.

While illustrated herein below in the context of the pretreated composition generated in acid hydrolysis system 110, it is noted that the liquefaction system 202 can be used with a wide variety of lignocellulosic biomass compositions. Liquefaction system 202 is considered tolerant to lignocellulosic biomass compositions having a wide range of consistencies. Advantageously, a relatively under-treated composition having a relatively rigid-like consistency can be fed to liquefaction system 202 and be processed into a relatively more pumpable composition using a wide variety of pumps. At the same time, a relatively over-treated composition having a mud-like consistency can be fed to the same liquefaction system 202 and pumped using the same pumping equipment as with an under-treated composition that may be fed to liquefaction system 202. Nonlimiting examples of lignocellulosic biomass compositions that can be fed to liquefaction system 202 include grasses, wood chips and pulp, and various cereal straws, including the pretreated corn stover described herein throughout. While not being bound by theory, it is believed that a liquefaction system configuration described herein utilizes a combination of 1) retention time in liquefaction tanks, 2) separation devices, 3) optional grinding and 4) recirculation to provide a system that is robust to input streams having a wide range of consistencies in terms of the physical structure of lignocellulosic biomass.

The liquefaction system 202 is configured to enzymatically hydrolyze at least a portion of the cellulose into oligosaccharides and glucose to facilitate at least partial structural breakdown of the pretreated composition and form a liquefied composition.

Liquefaction system 202 can include at least one slurry tank 210 configured to receive a stream 201 of lignocellulosic biomass composition such as the pretreated composition from flash tank system 120. In some embodiments, slurry tank 210 can be a continuously mixed reactor such as continuously stirred tank reactor (CSTR). The slurry tank can be configured to combine an alkaline source with the pretreated composition to adjust the pH of the pretreated composition and combine one or more enzymes (e.g., an enzyme cocktail) with the pretreated composition. Nonlimiting examples of enzymes include cellulase enzymes and hemicellulose enzymes.

Liquefaction system 202 can include also include one or more liquefaction tanks 225 (individual tanks not shown) for receiving the pretreated composition from slurry tank 210 and configured to maintain the pretreated composition at a pH and temperature for a time period to convert at least a portion of one or more polysaccharides such as cellulose in the pretreated composition into oligosaccharides and/or glucose. In some embodiments, one or more liquefaction tanks 225 can include two or more, three or more, four or more, or even five or more liquefaction tanks. A nonlimiting example of a liquefaction tank includes a continuously mixed reactor (e.g., a continuous stirred tank reactor (CSTR)). In some embodiments, the one or more liquefaction tanks are connected in series so that the contents of an upstream tank continuously feed an adjacent downstream tank. In some embodiments, the series of two or more tanks can include a recycle pipeline 244 to recycle at least a portion of the pretreated composition back through the series of one or more liquefaction tanks so as to form a continuous recycle loop. In some embodiments, the temperature of the pretreated composition during at least a portion of liquefaction is in a range from 110° F. to 150° F., or even from 120° F. to 140° F. In some embodiments, the pH of the pretreated composition during at least a portion of liquefaction is in a range from 4 to 6, or even from 4.5 to 5.5. In some embodiments, the residence time of the pretreated composition in the one or more liquefaction tanks is at least 2 hours. In some embodiments, the residence time of the pretreated composition in the one or more liquefaction tanks is in the range from 2 to 25 hours, or even from 6 to 10 hours. Liquefaction systems are described, e.g., in U.S. Pub. No. 2013/0065289 (Carlson), which patent document is incorporated herein by reference.

The liquefaction system 202 can also include one or more separation devices in fluid communication with the liquefied composition. As shown in FIG. 2, separation device 230 is in fluid communication with the liquefied composition from the one or more liquefaction tanks 225. Separation device 230 can be configured to separate at least a portion of the liquefied composition into a solid fraction (retentate) and a liquid fraction (filtrate). It is noted that the solid fraction and liquid fraction each have a liquid component and a solid component. The solid fraction (retentate) has a higher concentration of solid component as compared to the liquid fraction (filtrate) and the stream that is fed to the separation device 230. Also, both the liquid fraction and the solid fraction can both include cellulose, hemicellulose, oligosaccharides, glucose and xylose.

The solid fraction can include dissolved solids and undissolved solids such as unhydrolyzed lignocellulosic biomass. The size of the undissolved solid particles in the liquid fraction depends on the separation device that is selected. In some embodiments, as shown in FIG. 2 for illustration purposes, the separation device 230 includes a gravity screen device so the size of the undissolved solid particles in the liquid fraction depends on the size of the openings in the separation device 230. The size of the screen at least for gravity screen 230 can be selected so that the particle size of the solid material in liquid fraction 231 is small enough so that the liquid fraction can pass through a heat exchanger without undue clogging. In some embodiments, a separation device 230 can include a gravity screen having a screen opening size of about 0.25 inches or less, 0.2 inches or less, 0.150 inches or less, or even 0.125 inches or less. Gravity screens are commercially available from SWECO under the tradename STA-SIEVE stationary screening device having model number SV10S BB.

As shown in FIG. 2, separation device 230 separates liquefied composition from liquefaction tanks 225 into a solid fraction 260 and liquid fraction 231. Liquid fraction 231 can be a highly pumpable composition using a wide variety of commercially available pumps, even when compositions fed to liquefaction system 202 have a wide range of consistencies; for example, lignocellulosic material ranging from material having a rigid-like consistency to material that has been degraded into a mud-like consistency.

Liquid fraction 231 can be divided into two or more liquid streams. As shown, liquid fraction 231 is divided into stream 232 and stream 245.

Liquid stream 232 can be sent to one or more saccharification tanks 250 in saccharification system 203. The saccharification system 203 can be configured to enzymatically hydrolyze polymers, e.g., cellulose, in liquid stream 232 into sugars, e.g., glucose, or oligomers thereof, and form a saccharified composition. In some embodiments, saccharification tanks 250 can include one or more batch reactors (not shown) in series or parallel communication with liquid stream 232 to receive liquid stream 232. The saccharification tanks 250 can also be configured to maintain their contents at a pH and a temperature for a time period to convert at least a portion of the oligosaccharides and polysaccharides into glucose. In some embodiments, the temperature of the reactor contents can be in a range from 110° F. to 150° F., or even from 120° F. to 140° F. In some embodiments, the pH of the reactor contents be in a range from 4 to 6, or even from 4.5 to 5.5. In some embodiments, the saccharification time period is in the range from 48 to 120 hours, or even from 112 to 114 hours.

As shown in FIG. 2, liquid stream 245 passes through heat exchanger system 280 to cool liquid stream 245 so that the cooled liquid stream 245 may be combined with pretreated composition 201 (e.g., as provided from flash tank system 120 described in FIGS. 1A and 1B above). The liquid stream 245 can be cooled ("sub-cooled" below even liquefaction temperature) to a temperature that is sufficient to cool the pretreated composition to a temperature that permits enzymatic hydrolysis in the liquefaction system 202. The temperature of the stream to slurry tank 210 after combining the pretreated composition 201 and liquid stream 245 can be in a range from 110° F. to 150° F., or even from 120° F. to 140°

F. One or more additional liquid streams can be created after passing through a separation device, and cooled if desired, to use as desired.

Exemplary heat exchanger systems include shell and tube heat exchanger systems, plate and frame heat exchanger systems, and the like. As shown in FIG. 2, solid fraction 260 is recycled to slurry tank 210 until the solid fraction particles are reduced in size such that they pass through gravity screen 231 and ultimately to saccharification system 203. Advantageously, separating and recycling is a simple and effective approach to sufficiently breaking down solid fraction 260 (e.g., due to enzyme action) for saccharification. Grinding devices can be avoided if desired. However, if desired one or more optional size reduction devices 261 such as a disc mill can be used to grind over-sized solid material that is present in solid fraction 260.

As shown in FIGS. 1A and 1B, after enzymatic hydrolysis system 150, the saccharified composition be fed into fermentation system 160 so that a microorganism such as yeast can convert sugars, e.g., xylose and glucose, into a biochemical such as ethanol. After fermentation, the beer from fermentation system 160 can be fed to distillation system 170 to recover a biochemical such as ethanol.

EXAMPLES

Example 1

Figure 4A:
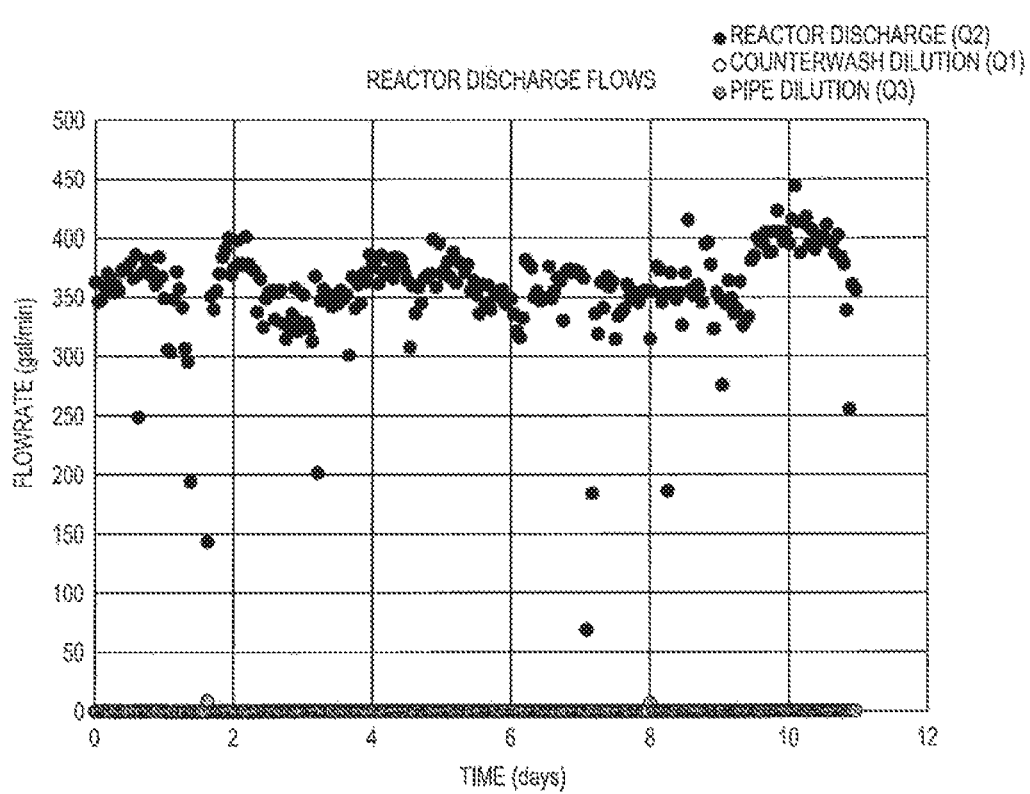
FIG. 4A shows a graph of reactor discharge flow for Example 1.
Figure 4B:
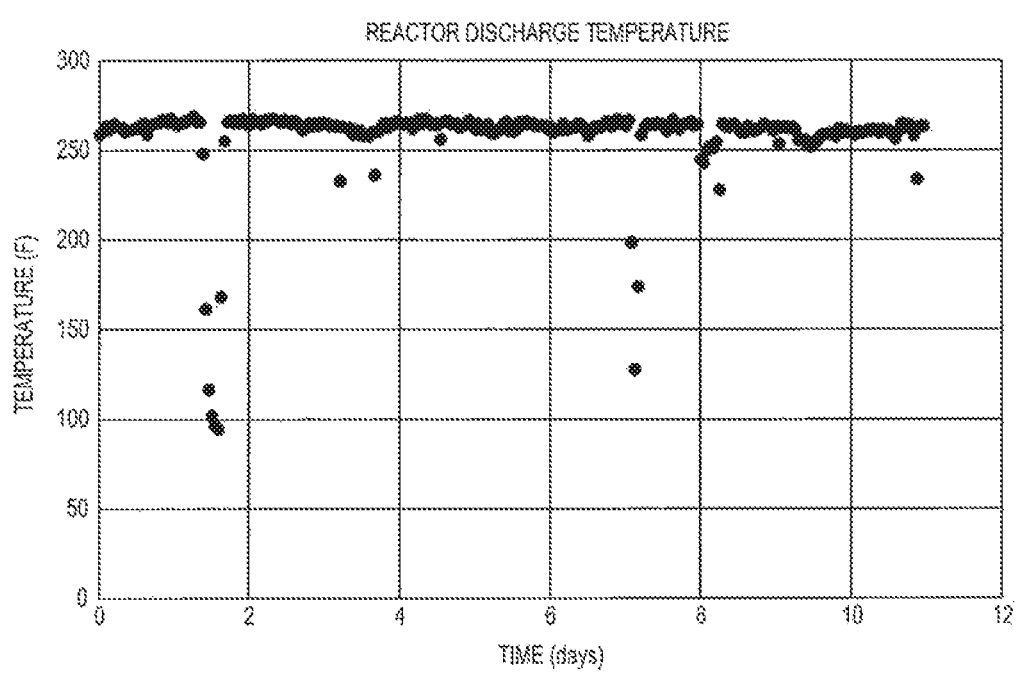
FIG. 4B shows a graph of reactor discharge temperature for Example 1.
Figure 4C:
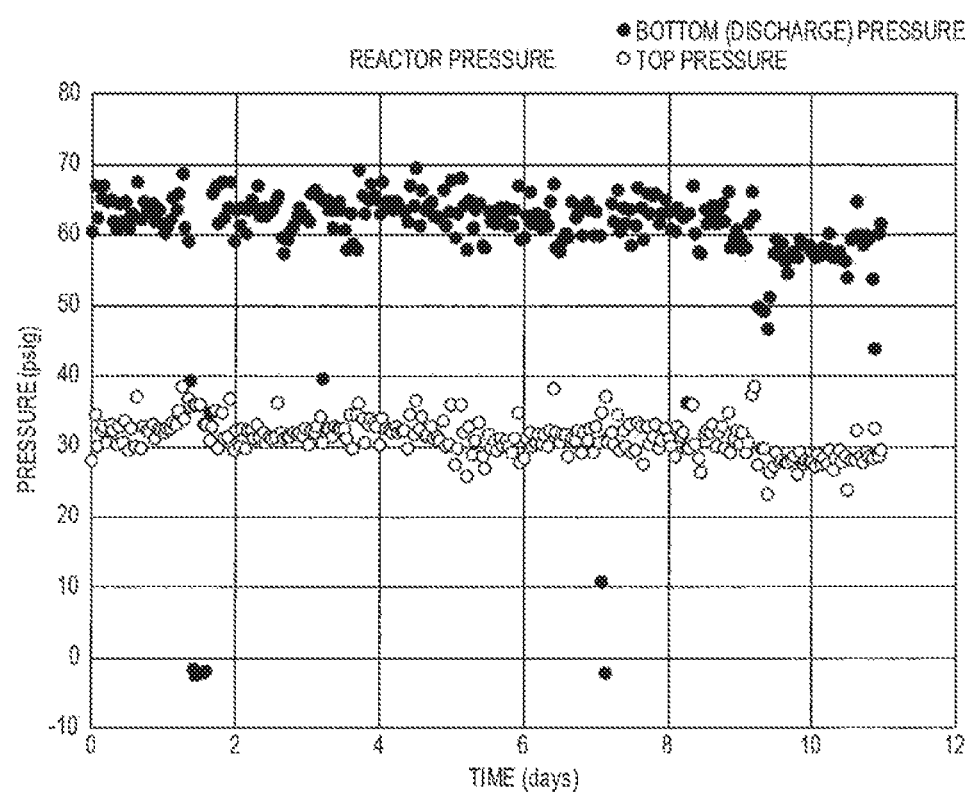
FIG. 4C shows a graph of reactor pressure for Example 1.
Figure 4D:
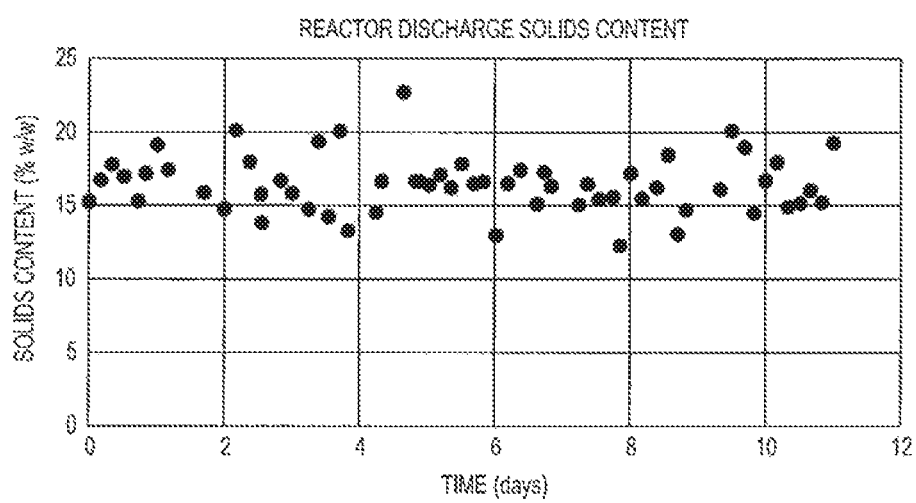
FIG. 4D shows a graph of reactor discharge solids content for Example 1.

Referring to FIG. 1A, pretreatment reactor in system 110 was operated to pretreat ground corn stover at steady state with minimal downtime for a period of eleven days with the reactor discharge stream 106 going directly to a flash cyclone in system 120. Sulfuric acid was added to adjust the pH of the aqueous phase of the slurry feeding into the pretreatment reactor to approximately 1.5. During this time period the discharge rate was an average of 361.7 gallons per minute with a standard deviation of +/−104.9 gpm when running (FIG. 4A). The temperature of the reactor discharge stream was 262.4 F with a standard deviation of +/−5.7 F during this time period when running (FIG. 4B). The solids content of the reactor discharge stream was an average of 16.4% w/w with a standard deviation of +/−1.9% w/w (FIG. 4D). The pressure at the top of the reactor was an average of 31.4 psig with a standard deviation of +/−3.2 psig, and the pressure of the discharge stream at the bottom of the reactor was an average of 62.3 psig with a standard deviation of +/−4.0 psig (FIG. 4C). No dilution of the reactor discharge stream was necessary or used during the duration of this trial except for incidental use during startup or shutdown (i.e., there were no dilution streams 101 or 104 as shown in FIG. 1B).

Example 2

Figure 5:
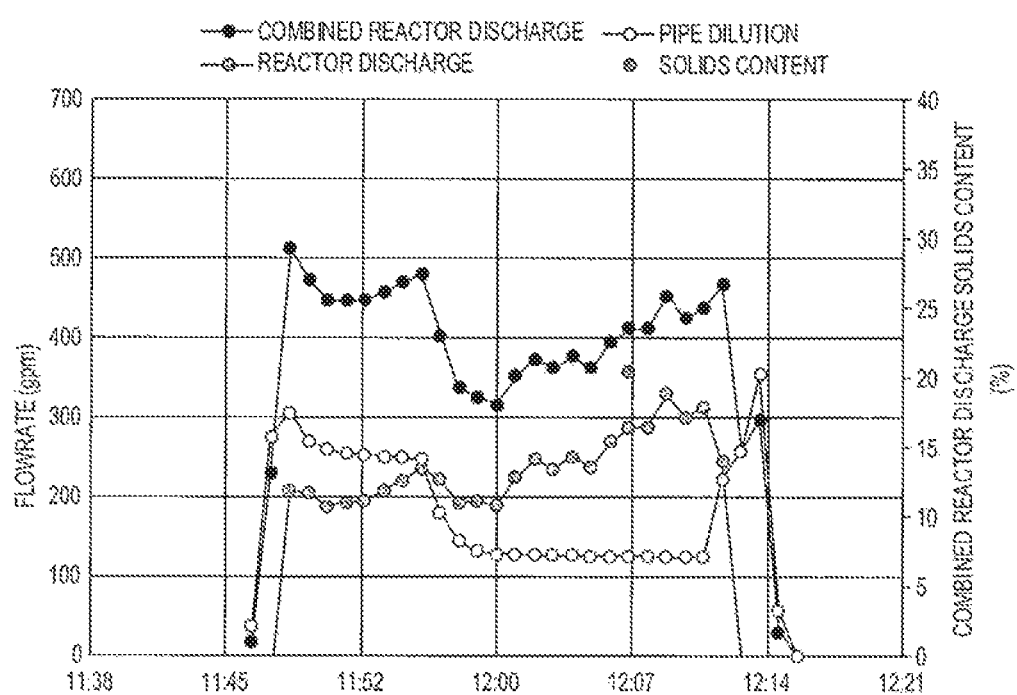
FIG. 5 shows a graph related to Example 2.

Referring to FIG. 1B, a pretreatment reactor in acid hydrolysis system 110 was operated to pretreat corn stover. Sulfuric acid was added to adjust the pH of the aqueous phase of the slurry feeding into the pretreatment reactor to approximately 1.5. In this example, a desirable high solids level was achieved while adding a pipe dilution stream 104 to the reactor discharge stream to form combined stream 106. FIG. 5 shows the flowrate of the combined reactor discharge stream 106 and what portion of the combined stream was reactor discharge and what portion was pipe dilution stream 104. During this test the combined reactor discharge was made up of between 40%-70% reactor discharge and the balance from stream 104. The average solids content of stream 106 achieved during this test was 20.4%.

What is claimed is:

1. A system configured to process lignocellulosic biomass, wherein the system comprises:
    a) a source of lignocellulosic biomass;
    b) an pretreatment system in fluid communication with the source of lignocellulosic biomass, wherein the pretreatment system comprises at least one reactor configured to expose the lignocellulosic biomass to conditions to form a pretreated composition comprising a liquid component and a solid component, wherein the reactor has a discharge outlet and the pretreated composition at the discharge outlet is at conditions comprising a pressure above the saturated vapor pressure of the pretreated composition, and a total solids content of 10 to 35 percent;
    c) a source of an aqueous stream in fluid communication with the at least one reactor to dilute the pretreated composition at the reactor discharge outlet and/or in fluid communication with pretreated composition discharged from the reactor discharge outlet to dilute the pretreated composition, wherein the aqueous stream is at a pressure in the range from 20 to 80 psig and at a temperature greater than 212° F.; and
    d) at least one flash tank system in fluid communication with the pretreatment system, wherein the flash tank system comprises a pressure reducing device coupled to a flash tank, wherein the pressure reducing device is configured to flash the pretreated composition from the conditions at the discharge outlet to a pressure less than the saturated vapor pressure of the pretreated composition at the discharge outlet, wherein the pretreated composition has less than three percent by volume of vapor space at least from the discharge outlet of the at least one reactor to an inlet of the pressure reducing device.

2. The system of claim 1, wherein the pretreated composition at the discharge outlet is at a temperature greater than 212° F., and wherein the pressure reducing device is configured to flash the pretreated composition from the conditions at the discharge outlet to a pressure of less than 1 psig.

3. The system of claim 1, wherein the discharge outlet of the reactor is in direct fluid communication with the pressure reducing device.

4. The system of claim 1, wherein the pretreatment system comprises an acid hydrolysis system, wherein the acid hydrolysis system comprises at least one acid hydrolysis reactor configured to expose the lignocellulosic biomass to an aqueous acid solution to form the pretreated composition.

5. The system of claim 4, wherein the acid hydrolysis reactor is configured to expose the lignocellulosic biomass to an aqueous acid solution at a pressure in the range from 20 to 80 psig, a temperature in the range from 245° F. to 275° F. and a pH in the range from 0.5 to 3.0 for a time period in the range from 0.5 to 5 hours to form the pretreated composition.

6. The system of claim 4, wherein the acid hydrolysis system comprises one acid hydrolysis reactor and the flash tank system comprises one flash tank, wherein the acid hydrolysis reactor and the flash tank can process 200 tons/day or more of ground corn cobs and ground corn stover.

7. The system of claim 1, further comprising an enzymatic hydrolysis system comprising:
    a) a liquefaction tank system, wherein the liquefaction system is in fluid communication with the flash tank system to receive the pretreated composition, wherein the liquefaction system is configured to enzymatically hydrolyze at least a portion of the pretreated composition to form a liquefied composition;
b) at least one separation device in fluid communication with the liquefied composition, wherein the separation device is configured to separate at least a portion of the liquefied composition into a solid fraction and a liquid fraction, wherein the at least one separation device comprises a gravity screen device having a screen opening size of about 0.25 inches or less; and
c) at least one heat exchanger system in fluid communication with at least a first portion of the liquid fraction, wherein the heat exchanger system is configured to cool the first portion of the liquid fraction to a temperature that is sufficient to cool the pretreated composition provided to the liquefaction system to a temperature that permits enzymatic hydrolysis in the liquefaction system, and recycle the cooled first portion of the liquid fraction so that the cooled first portion of the liquid fraction is combined with pretreated composition provided to the liquefaction system.

8. The system of claim 4, wherein the source of the aqueous stream comprises at least a first aqueous stream having a first flow rate (Q1) in fluid communication with the acid hydrolysis reactor to dilute the pretreated composition so that the pretreated composition at the reactor discharge outlet has a total solids content of 10 to 35 percent, wherein the pretreated composition into the inlet of the pressure reducing device has a second flow rate (Q2), wherein 0≤Q1<Q2, and wherein the first aqueous stream is at a pressure in the range from 20 to 80 psig and at a temperature in the range from 245° F. to 275° F.

9. The system of claim 8, wherein the acid hydrolysis reactor comprises at least one separation device to separate liquid from solid lignocellulosic biomass and form the first aqueous stream.

10. The system of claim 8, wherein the at least one acid hydrolysis reactor is a vertical reactor having an inlet to receive the source of lignocellulosic biomass, wherein the inlet is located proximal to the top of the acid hydrolysis reactor and the discharge outlet is located proximal to the bottom of the of acid hydrolysis reactor, wherein the acid hydrolysis reactor comprises an agitation system comprising an agitation device located proximal to the discharge outlet to agitate the pretreated composition.

11. The system of claim 8, further comprising at least a second aqueous stream having a third flow rate (Q3) in fluid communication with the pretreated composition from the acid hydrolysis reactor discharge outlet to dilute the pretreated composition so that the pretreated composition has a total solids content of 10 to 35 percent, wherein 0≤Q3<0.5*Q2, and wherein the second aqueous stream is at a pressure in the range from 20 to 80 psig and at a temperature in the range from 245° F. to 275° F.

12. The system of claim 7, wherein the enzymatic hydrolysis system further comprises:
a) at least one slurry tank in direct fluid communication with the flash tank system to receive the pretreated composition, wherein the slurry tank is configured to adjust the pH of the pretreated composition and add one or more enzymes to the pretreated composition; and
b) a saccharification system that is in fluid communication with a second portion of the liquid fraction, wherein the saccharification system is configured to enzymatically hydrolyze the second portion of the liquid fraction to form a saccharified composition.

13. The system of claim 1, wherein the source lignocellulosic biomass comprises ground corn cobs and ground corn stover having a particle size such that at least 80 percent of the ground corn cobs and ground corn stover passes through a six inch screen and less than 20 percent of the ground corn cobs and ground corn stover passes through a 0.125 inch screen.

14. The system of claim 1, wherein the aqueous stream is at a temperature in a range from 245° F. to 302° F.

15. The system of claim 1, wherein the aqueous stream is at a temperature in a range from 245° F. to 280° F.

16. A system configured to process lignocellulosic biomass, wherein the system comprises:
a) a source of a pretreated composition derived from lignocellulosic biomass;
b) a liquefaction system, wherein the liquefaction system is in fluid communication with the pretreated composition, wherein the liquefaction system comprises an inlet and is configured to enzymatically hydrolyze at least a portion of the pretreated composition to form a liquefied composition, wherein the liquefaction system comprises two or more liquefaction tanks connected in series so that the contents of an upstream liquefaction tank feeds an adjacent downstream liquefaction tank, wherein the residence time of the pretreated composition in the two or more liquefaction tanks is at least 2 hours;
c) at least one separation device in fluid communication with the liquefied composition, wherein the separation device is configured to separate at least a portion of the liquefied composition into a solid fraction and a liquid fraction;
d) at least one heat exchanger system in fluid communication with at least a first portion of the liquid fraction, wherein the heat exchanger system is configured to cool the first portion of the liquid fraction to a temperature that is sufficient to cool the pretreated composition provided to the liquefaction system to a temperature that permits enzymatic hydrolysis in the liquefaction system, and recycle the cooled first portion of the liquid fraction so that the cooled first portion of the liquid fraction is combined with the pretreated composition provided to the liquefaction system; and
e) at least one recycling system in fluid communication with at least a portion of the solid fraction, wherein the recycling system is configured to recycle the portion of the solid fraction to the inlet of the liquefaction system.

17. The system of claim 16, wherein the at least one recycling system comprises a size reduction mechanism configured to reduce the particle size of the solid fraction.

18. The system of claim 16, wherein the at least one recycling system does not include a size reduction mechanism.

19. The system of claim 16, wherein the at least one separation device comprises a gravity screen having a screen opening size of 0.125 inches or less.

20. The system of claim 16, wherein the two or more liquefaction tanks comprise two or more continuously mixed liquefaction reactors.

* * * * *